United States Patent [19]

Deneke et al.

[11] Patent Number: 4,603,107
[45] Date of Patent: Jul. 29, 1986

[54] REAGENT AND PROCESS FOR THE DETERMINATION OF THE ACTIVITY OF THE ENZYME GAMMA-GLUTAMYL TRANSFERASE

[75] Inventors: Ulfert Deneke, Mörlenbach; Rolf Nagel, Bürstadt; Walter Rittersdorf, Mannheim, all of Fed. Rep. of Germany

[73] Assignee: Boehringer Mannheim GmbH, Mannheim, Fed. Rep. of Germany

[21] Appl. No.: 532,907

[22] Filed: Sep. 16, 1983

[30] Foreign Application Priority Data

Sep. 17, 1982 [DE] Fed. Rep. of Germany ....... 3234478

[51] Int. Cl.$^4$ .................... C12Q 1/00; C12Q 1/28; C12Q 1/36; C12Q 1/48
[52] U.S. Cl. ........................ 435/15; 435/4; 435/24; 435/28; 435/805; 435/810
[58] Field of Search ................ 435/15, 24, 28; 435/4, 435/805, 810

[56] References Cited

U.S. PATENT DOCUMENTS

| | | | |
|---|---|---|---|
| 2,905,594 | 9/1959 | Morris | 435/28 |
| 4,177,109 | 12/1979 | Tohyama et al. | 435/24 |
| 4,425,427 | 1/1984 | Luderer | 435/10 |
| 4,511,651 | 4/1985 | Beaty et al. | 435/15 |

OTHER PUBLICATIONS

Bergmeyer, *Methoden der Enzymatischen Analyse*, vol. I, (1974), Verlag Chemie, Weinheim, pp. 757–759 and 761.

*Primary Examiner*—Robert J. Warden
*Assistant Examiner*—Patricia K. White
*Attorney, Agent, or Firm*—Felfe & Lynch

[57] ABSTRACT

The present invention provides a process for the kinetic determination of $\gamma$-glutamyl transferase activity by the reaction of a $\gamma$-glutamylarylamide with the formation of an arylamine at a pH value of from 6 to 10, wherein the arylamine is simultaneously reacted with an aromatic amine or phenol appropriate as a coupling component and an appropriate oxidation agent to give a colored compound with an absorption maximum above 565 nm, the rate of formation of which is monitored photometrically and is used as a measure for the $\gamma$-glutamyl transferase activity.

The present invention also provides a reagent for the kinetic determination of $\gamma$-GT activity, wherein it contains the following reagents:
$\gamma$-GT-arylamide:1–100 mmol/l.
$\gamma$-glutamyl acceptor (glycylglycine):10–500 mmol/l.
coupling component:1–500 mmol/l.
oxidation agent:0.1–500 mmol/l.
buffer:10–1000 mmol/l.

10 Claims, 1 Drawing Figure

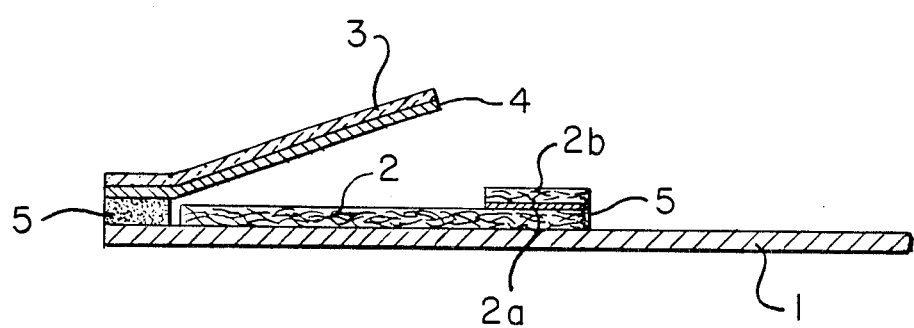

REAGENT AND PROCESS FOR THE DETERMINATION OF THE ACTIVITY OF THE ENZYME GAMMA-GLUTAMYL TRANSFERASE

The present invention is concerned with a reagent and a process for the determination of the activity of the enzyme γ-glutamyl transferase (γ-GT, γ-glutamyl transpeptidase, EC No. 2.3.2.2) in whole blood, plasma, serum, biological fluids or other materials, using an appropriate γ-glutamylarylamide as substrate, the arylamine liberated by the γ-GT reaction with an acceptor molecule being converted by means of an appropriate coupling component and an appropriate oxidation agent into a coloured material, the formation of which can be monitored kinetically.

Since the discovery of γ-GT in the human serum, this enzyme has achieved a great importance, especially in liver diagnosis (see H. U. Bergmeyer, Methoden der Enzymatischen Analyse, Volume I, pub. Verlag Chemie, Weinheim, 1974, pages 14–30 and 757). For the determination of the activity of γ-GT in a sample, there is usually determined the rate of the reaction of a γ-glutamylamide with glycylglycine as acceptor, with the formation of γ-glutamylglycylglycide and an amine. These methods of determination can be divided into two classes, on the one hand, into those in which the liberated amine itself is a chromogenic substrate and, on the other hand, into those in which the liberated amine is first converted into a coloured compound by subsequent reactions.

The first group includes various nitroaniline derivatives, the amine group of which is linked to a γ-glutamyl radical. By the transfer of the γ-glutamyl radical to an acceptor molecule, the nitroaniline is liberated, the extinction maximum of which is bathochromically displaced with regard to the starting compound so that the colour increase can be measured at appropriate wavelengths in the yellow and red range. Known chromogenic substrates for γ-GT include, in particular, γ-glutamyl-p-nitroanilide and γ-glutamyl-p-nitroanilide-3-carboxylic acid. Less usual is γ-glutamyl-p-nitroanilide-3-sulphonic acid. These substrates permit kinetic measurements and single point measurements.

The second group includes the substrates γ-glutamylaniline, γ-glutamyl-α-naphthylamine, γ-glutamyl-β-naphthylamine, γ-glutamyl-p-hydroxyaniline and variously substituted derivatives thereof. These are used in such a manner that the arylamine liberated by the γ-GT reaction is converted into a measurable coloured material by means of oxidative coupling, condensation with an aromatic aldehyde or diazonium salt coupling. The γ-GT reaction is thereby carried out for a definite period of time and then, with the addition of an acid or base, the colour reaction is carried out, the γ-GT reaction thereby being stopped (single point measurement) (see, for example, published Federal Republic of Germany Patent Specifications Nos. 29 20 292 and 23 38 043). A kinetic measurement is not possible according to this method since the liberation of the amine and the colour formation cannot be carried out under the same conditions.

Further methods of determination of γ-GT described in the literature have achieved practically no importance because they are laborious and difficult to carry out.

The above-described processes involve serious deficiencies which limit their use, especially when the γ-GT reaction is to be carried out on test strips since a visual evaluation is only possible when the light absorption takes place in a sufficiently long-waved range. Even when test strips are to be evaluated by remission photometry, light must be used with a wavelength of more than 565 nm since biological materials, such as plasma, serum or urine, contain a number of substances which absorb in the shorter wavelength range and thus the measurement would be negatively influenced. However, the previously known chromogenic substrates of γ-GT can only be measured at the highest up to 500 nm. Here, however, bilirubin in particular still absorbs very strongly so that even in a photometric test, which includes a dilution of the sample, often the whole measurement range of the photometer is used up by the inherent absorption of the sample. Furthermore, the spectra of the γ-glutamylated substrate and of the liberated chromogen mostly overlap so considerably that it is only possible to measure in the band flanks of the chromogen or the initial extinction of the reagent is already very high. This means that especially high requirements are demanded of the quality of the photometer and the sensitivity of the methods is limited. However, it is an advantage of chromogenic substrates that they permit a kinetic measurement. This is of importance especially for test strips because here practically only kinetic measurements can be evaluated simply and meaningfully by remission photometry.

The coloured materials obtained in the known γ-GT tests by oxidative coupling, aldehyde condensation or diazonium salt coupling are, as a rule, red, violet or blue and, therefore, present no problems with the sample blank. Here, however, it is exclusively a question of end point determinations and these, in turn, cannot be rationally realised in test strips.

Consequently, it is an object of the present invention to provide a γ-GT test in which a coloured material formation can be measured kinetically, the coloured material thereby formed having its absorption maximum at above 565 nm.

Thus, according to the present invention, there is provided a process for the kinetic determination of γ-glutamyl transferase activity by the reaction of a γ-glutamylarylamide with the formation of an arylamine at a pH value of from 6 to 10, wherein the arylamine is simultaneously reacted with an aromatic amine or phenol appropriate as a coupling component and an appropriate oxidation agent to give a coloured compound with an absorption maximum above 565 nm, the rate of formation of which is monitored photometrically and is used as a measure for the γ-glutamyl transferase activity.

If desired, the process according to the present invention can also be carried out on test strips.

Even the first publication on the characterisation of γ-GT stated that it is a glycoprotein which also contains essential SH groups (see A. Szewczuk and T. Baranowski, Biochem. Z., 338, 317–329/1963). Such compounds are normally irreversibly changed by oxidation agents. For the enzyme treated with periodate, this inhibition or denaturing has already been described in the above-cited publication. This is apparently one of the reasons why all previously described γ-GT reactions depending upon oxidative coupling are only carried out as stop versions. A further reason is certainly that, in the optimum pH range for γ-GT, i.e. pH 6 to 10 and especially pH 7.5 to 8.5, the oxidation agents usually used for the oxidative coupling do not react or only react slowly.

Since, however, the coupling reaction must be rapid in comparison with the splitting reaction in order not to be rate-determining for the kinetic determination, the oxidative coupling was hitherto carried out either in an acidic or in an alkaline medium after splitting had taken place.

It is, therefore, highly surprising that there are oxidation agents which, at a pH of from 6 to 10, oxidise the amines so quickly that the activity of the γ-GT can be measured kinetically by a coupling reaction and, nevertheless, not cause irreversible damage to the γ-GT enzyme either on the sugar part or on the SH groups. Of the large number of oxidation agents, ferricyanide and peroxide or peroxide former/peroxidase are the only ones which have hitherto been found to be usable, the first being preferred.

The substrate used can be a γ-glutamyl derivative of aniline, naphthylamine, 2-hydroxy-4-aminobenzoic acid and other compounds which, in the case of the γ-GT reaction, give a coupling substrate. Especially preferred compounds are those of the general formula:

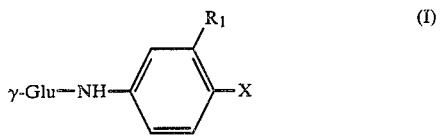

in which X is an $-NR_2R_3$ or $-O-R_2$ group, $R_1$ is a hydrogen atom, an alkoxy, alkyl or aryl radical containing up to 8 carbon atoms, a chlorine, bromine or iodine atom or an $-NR_2R_3$, $-SO_3R_2$ or $-COOR_2$ group, and $R_2$ and $R_3$, which are the same or different, are hydrogen atoms or alkyl or aryl radicals containing up to 8 carbon atoms, which can also be substituted by OH, alkoxy, COOH or $SO_3H$.

Such compounds and processes for the preparation thereof are described, for example, in published Federal Republic of Germany Patent Specification No. 28 23 342.

An especially preferred substrate is γ-glutamyl-p-phenylenediamine-3-carboxylic acid, which has hitherto not been described in the literature and which is best obtained by the reduction of γ-glutamyl-4-nitroaniline-3-carboxylic acid.

As coupling components, there can be used the substrates known for this reaction, i.e. aromatic amines or phenols, which are also described in the above-mentioned published Federal Republic of Germany Patent Specification No. 28 23 342. Especially preferred are compounds of the general formula:

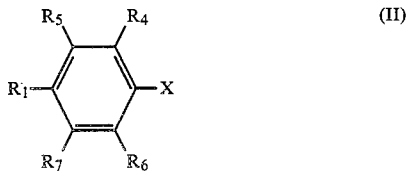

in which X is an $NR_2R_3$ or $-O-R_3$ group, $R_1$ is a hydrogen atom or a chlorine atom, when $R_4$ and/or $R_6$ are also chlorine atoms, $R_2$ and $R_3$, which are the same or different, are hydrogen atoms or alkyl, aralkyl or aryl radicals containing up to 8 carbon atoms, which can possibly also be substituted by hydroxyl, alkoxy containing up to 5 carbon atoms, $-COOH$ or $-SO_3H$, $R_4$ and $R_6$, which are the same or different, are hydrogen atoms, alkyl radicals containing up to 5 carbon atoms, chlorine, bromine or iodine atoms or $-COOR_2$, $SO_3R_2$, $OR_2$ or $NR_2R_3$, $R_2$ and $R_3$ having the above-given meanings, $R_5$ and $R_7$, which are the same or different, are hydrogen or alkyl radicals containing up to 5 carbon atoms, or $R_4$ and $R_5$ or $R_6$ and $R_7$, together with the benzene ring, can also form a naphthyl or anthryl structure.

The alkyl radicals in the above compounds contain up to 6 and preferably up to 3 carbon atoms, the methyl radical being especially preferred. Thus, especially preferred compounds include 2,3-xylenol, diethylmethanilic acid, N-ethyl-N-(3'-sulphobenzene)aniline and N-methylanthranilic acid.

Besides the components necessary for the actual reaction, i.e. γ-glutamylarylamide, acceptor (glycylglycine), coupling component, oxidation agent and buffer substance (pH 6 to 10), the reagents according to the present invention can also contain activators (e.g. magnesium salts), wetting agents, stabilising agents, thickening agents and other conventional adjuvants. The test can be carried out either as usual in a cuvette or also on an absorbent carrier (test strip) which has been impregnated with the reagents.

For a conventional test batch in a standard cuvette with 10 mm. layer thickness and a test volume of 2 to 3 $cm^3$, an amount of blood or serum of 20 to 100 μl. is needed and, in the case of micro-cuvettes, correspondingly less. The reagent solution has approximately the following composition, in each case in mmol/l. of solution:

1-100 γ-glutamylarylamide
10-200 acceptor molecule (e.g. glycylglycine)
1-200 coupling component
0.1-100 oxidation agent
10-200 buffer (pH 6-10).

Furthermore, there can also be present
0-10 activator (e.g. magnesium salt)
0-10 wetting agent
0-50 stabilising agent
0-100 thickening agent.

For the test on absorbent carriers, a droplet of serum or plasma (10-50 μl.) can be applied to the dry carrier impregnated with the reagents.

Because of the small layer thickness which is available for the evaluation, the reagent solutions used for the impregnation should be somewhat more concentrated than in the case of the cuvette test. The following compositions in mmol/l. can be used:

5-100 γ-glutamylarylamide
50-500 glycylglycine
10-500 coupling component
1-500 oxidation agent
50-1000 buffer (pH 6-10 and especially 7.5-8.5)

as well as the other substances described for the cuvette test in the given amounts. The γ-glutamylarylamides, coupling components and oxidation agents which can be used have already been described above. As buffers, there can be used all conventional weakly alkaline buffers which are effective in the given pH range. EDTA, tris buffer, 2-amino-2-methylpropane-1,3-diol and the like are preferred since, at the same time, they also have heavy metal-complexing properties. As activators for the enzyme, there are advantageously added magnesium salts, for example magnesium chloride or the like, in small amounts.

BRIEF DESCRIPTION OF THE DRAWING

The drawing shows a test strip embodiment of the invention.

The following Examples illustrate the invention:

EXAMPLE 1

Cuvette test for γ-GT tris.HCl, pH 8.0: 100 mmol/l.
γ-glutamyl-p-phenylenediamine-3-carboxylic acid: 10 mmol/l.
glycylglycine: 75 mmol/l.
N-methylanthranilic acid: 50 mmol/l.
potassium ferricyanide: 0.5 mmol/l.
solvent: water To 3 ml. of this solution are added 50 μl. of human serum and measured at a layer thickness of 10 mm. and a wavelength of 60–800 nm. V=3.05 ml., v=0.05, T 37° C., λ=630 nm. ε=18.4 cm²/mmol $$\frac{U}{l} = \frac{V \cdot \Delta E/\text{min.} \cdot 1000}{\epsilon \cdot v}$$

| U/liter | Δ E/min. |
| --- | --- |
| 0 | 0 |
| 10 | 3 |
| 20 | 6 |
| 50 | 15 |
| 100 | 30 |
| 200 | 60 |
| 500 | 150 |

EXAMPLE 2

Test strips for γ-GT

For the production of test strips, 2 papers are impregnated.

(A) Substrate Paper tris, pH 7.6: 200 mmol/l.
N-methylanthranilic acid: 100 mmol/l.
glycylglycine: 250 mmol/l.
EDTA-Na$_2$: 100 mmol/l.
γ-glutamyl-p-phenylenediamine-3-carboxylic acid: 20 mmol/l.
in water A paper of appropriate thickness and absorbency, for example teabag paper of the firm Schöler and Hoesch, 12 g./cm² surface weight, 50 μm. thickness, 50 ml./m. absorbency volume, is impregnated with this solution and dried for 5 minutes at 30° C. The paper is subsequently cut up into strips of 1 cm. width.

(B) Oxidation Paper potassium ferricyanide: 300 mmol/l.
in water

A paper similar to the substrate paper is impregnated with this solution, dried in an analogous manner and cut up into strips of 6 mm. width.

The material is worked up in an especially advantageous way into test strips such as are described in published Federal Republic of Germany Patent Specification No. 31 30 749 (see the accompanying drawing). A 1 cm. wide, transparent polycarbonate film of 110 μm. thickness is thereby fixed, together with the substrate paper, on one side on to a plastics strip so that the film is on the outside. In addition, a 15 mm. wide glass fibre fleece with a thickness of 1.5 mm. and a fibre strength of about 2 μm., is applied so that the free ends of the film and of the substrate paper still extend 6 mm. over the fleece. Bound to the other end of the glass fibre fleece is the oxidation paper and a 6 mm. wide strip of the same glass fibre material fixed on to the glass fibre fleece. The assembly is then cut up into 6 mm. wide test strips. In the single FIGURE of the accompanying drawing, the reference numerals have the following meanings:

1—carrier foil
2—glass fibre fleece, 15 mm. wide
2a—oxidation paper
2b—glass fibre fleece, 6 mm. wide
3—transparent foil
4—substrate paper
5—adhesive If 30 μl. of whole blood are now applied to the glass fibre 2b, then, within 30 to 60 seconds, the plasma portion penetrates the whole of the glass fibre fleece 2 and simultaneously dissolves the potassium ferricyanide from the oxidation paper, whereas the erythrocytes are retained in and under 2b. By applying pressure to the transparent foil, the γ-GT in the plasma and the oxidation agent now come into contact with the substrate paper, which is uniformly moistened through. Depending upon the concentration of the γ-GT and of the reaction time, there is formed a more or less marked green coloration, the change of intensity of which is proportional to the enzyme activity and can possibly be measured in a remission photometer between 565 and 850 nm. Naturally, other sample materials, such as plasma, serum and other biological materials can be used in an equal amount.

This arrangement proves to be especially advantageous because, in the phase of obtaining the plasma, bilirubin is already oxidised to biliverdin. This reaction would otherwise run together with the γ-GT reaction and, since biliverdin absorbs at 630 nm., would disturb the kinetics.

It will be understood that the specification and examples are illustrative but not limitative of the present invention and that other embodiments within the spirit and scope of the invention will suggest themselves to those skilled in the art.

What is claimed is:

1. Process for the kinetic determination of gamma-glutamyl transferase (gamma-GT) activity by the reaction of a gamma-glutamylarylamide substrate (gamma-GT substrate) with a gamma-glutamyl acceptor and gamma-GT comprising simultaneously combining the gamma-GT substrate with an oxidation agent, gamma-GT, an aromatic amine coupling component or a phenol coupling component, and a gamma-glutamyl acceptor said combination taking place at a pH of from about 6 to 10, said gamma-GT substrate forming an arylamine which reacts with said coupling component to give a colored compound with an absorption maximum above 565 nm, and photometrically monitoring the rate of formation of said colored compound as a measure of activity of the gamma-GT.

2. The process of claim 1 wherein the oxidation agent is a ferricyanide or a peroxide/peroxidase.

3. The process of claim 1 wherein the gamma-GT substrate is a compound of the formula

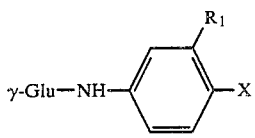

wherein

X is an —NR₂R₃ or —O—R₂ group;

R₁ is hydrogen; alkoxy, alkyl or aryl containing up to 8 carbon atoms; chlorine, bromine or iodine; or —NR₂R₃, —SO₃R₂ or —COOR₂; and R₂ and R₃, which are the same or different, are hydrogen; or substituted or unsubstituted alkyl or aryl containing up to 8 carbon atoms with substituents selected from the group consisting of OH, alkoxy, COOH and SO₃H.

4. A process as claimed in claim 1 wherein the coupling component is a compound of the formula

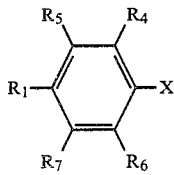

wherein

X is —NR₂R₃ or —O—R₃;

R₁ is hydrogen, or chlorine when R₄ and/or R₆ are also chlorine;

R₂ and R₃ are individually selected from the group consisting of hydrogen; or substituted or unsubstituted alkyl, aralkyl, or aryl containing up to 8 carbon atoms, with the substituent selected from the group consisting of hydroxyl, alkoxy containing up to 5 carbon atoms, —COOH or —SO₃H;

R₄ and R₆ are individually selected from the group consisting of hydrogen, alkyl containing up to 5 carbon atoms, chlorine, bromine, iodine, —COOR₂, —SO₃R₂, OR₂ and NR₂R₃, R₂ and R₃ having the above-given meanings; and R₅ and R₇ are individually selected from the group consisting of hydrogen or alkyl containing up to 5 carbon atoms; or R₄ and R₅ or R₆ and R₇, together with the benzene ring form a naphthyl or anthryl structure.

5. Process according to claim 1 wherein the coupling component is 2,3-xylenol, diethylmethanilic acid, N-ethyl-N-(3'-sulphobenzene)-aniline or N-methylanthranilic acid.

6. Process for the kinetic determination of gamma-glutamyl transferase (gamma-GT) activity by the reaction of a gamma-glutamylarylamide substrate (gamma-GT substrate) with a gamma-glutamyl acceptor and gamma-GT comprising simultaneously combining the gamma-GT substrate with an oxidation agent, gamma-GT, an aromatic amine coupling component or a phenol coupling component, and a gamma-glutamyl acceptor said combination taking place at a pH of from about 6 to 10, said gamma-GT substrate forming an arylamine which reacts with said coupling component to give a colored compound with an absorption maximum above 565 nm, and photometrically monitoring the rate of formation of said colored compound as a measure of activity of the gamma-GT, the gamma-GT substrate being a compound of the formula

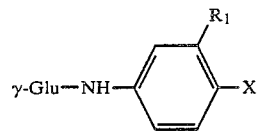

wherein

X is —NR₂R₃ or —O—R₂;

R₁ is hydrogen; alkoxy, alkyl or aryl containing up to 8 carbon atoms; chlorine, bromine or iodine; or —NR₂R₃, —SO₃R₂ or —COOR₂; and R₂ and R₃, which are the same or different, are hydrogen; substituted or unsubstituted alkyl or aryl containing up to 8 carbon atoms with substitutents selected from the group consisting of OH, alkoxy, COOH and SO₃H; and the coupling component being a compound of the formula

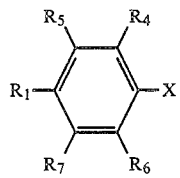

wherein

X is —NR₂R₃ or —O—R₃;

R₁ is hydrogen, or chlorine when R₄ and/or R₆ are also chlorine;

R₂ and R₃ are individually selected form the group consisting of hydrogen; or substituted or unsubstituted alkyl, aralkyl, or aryl containing up to 8 carbon atoms, with the substituent selected from the group consisting of hydrogen, alkyl containing up to 5 carbon atoms, chlorine, bromine, iodine, —COOR₂, —SO₃R₂, OR₂ and NR₂R₃, R₂ and R₃ having the above-given meanings; and R₅ and R₇ are individually selected from the group consisting of hydrogen or alkyl containing up to 5 carbon atoms; or R₄ and R₅ or R₆ and R₇, together with the benzene ring form a naphthyl or anthryl structure.

7. The process of claim 6 wherein the gamma-GT substrate is a gamma-glutamyl derivative of aniline, naphthylamine or 2-hydroxy-4-amino-benzoic acid.

8. The process of claim 1 wherein the gamma-GT substrate is gamma-glutamyl-p-phenylenediamine-3-carboxylic acid.

9. The process of claim 8 wherein the coupling component is 2,3-xylenol, diethylmethanilic acid, N-ethyl-N-(3'-sulphobenzene)-aniline or N-methylanthranilic acid.

10. The process of claim 6 wherein the coupling component is 2,3-xylenol, diethylmethanilic acid, N-ethyl-N-(3'-sulphobenzene)-aniline or N-methylanthranilic acid.

* * * * *